US008744819B2

(12) United States Patent
Rodriguez Y Baena

(10) Patent No.: US 8,744,819 B2
(45) Date of Patent: Jun. 3, 2014

(54) MODEL-BASED POSITIONAL ESTIMATION METHOD

(75) Inventor: Ferdinando Maria Rodriguez Y Baena, London (GB)

(73) Assignee: Mako Surgical Corp., Ft. Lauderdale, FL (US)

( * ) Notice: Subject to any disclaimer, the term of this patent is extended or adjusted under 35 U.S.C. 154(b) by 0 days.

(21) Appl. No.: 12/987,362

(22) Filed: Jan. 10, 2011

(65) Prior Publication Data

US 2011/0166832 A1 Jul. 7, 2011

Related U.S. Application Data

(63) Continuation of application No. 11/718,662, filed as application No. PCT/GB2005/004249 on Nov. 3, 2005, now abandoned.

(30) Foreign Application Priority Data

Nov. 4, 2004 (GB) .................................. 0424375.4

(51) Int. Cl.
G06G 7/48 (2006.01)
(52) U.S. Cl.
USPC ............... 703/6; 382/128; 382/243; 345/419; 345/629; 600/424; 600/301; 600/407; 600/429; 606/130; 606/63; 606/86 R
(58) Field of Classification Search
USPC ............ 702/167; 600/443, 439, 425; 128/898
See application file for complete search history.

(56) References Cited

U.S. PATENT DOCUMENTS

| 5,871,018 | A | * | 2/1999 | Delp et al. ..................... 128/898 |
| 5,880,976 | A | | 3/1999 | DiGioia et al. |
| 5,951,475 | A | * | 9/1999 | Gueziec et al. ............... 600/425 |
| 6,106,464 | A | * | 8/2000 | Bass et al. ..................... 600/439 |
| 2004/0015327 | A1 | * | 1/2004 | Sachdeva et al. ............. 702/167 |
| 2004/0068187 | A1 | * | 4/2004 | Krause et al. ................. 600/443 |

OTHER PUBLICATIONS

David Simon Fast and Accurate Shape-Based Registration Carnegie Mellon University, Dec. 12, 1996.*
International Search Report and Written Opinion for International Application No. PCT/GB2005/004249, mailed Feb. 2, 2006, 8 pages.
McKay et al, "A method for registration of 3-D shapes.", IEEE Transactions on pattern analysis and machine intelligence, 1992, 14(2):239-256.

(Continued)

Primary Examiner — Omar Fernandez Rivas
Assistant Examiner — Cuong Luu
(74) Attorney, Agent, or Firm — Foley & Lardner LLP

(57) ABSTRACT

A model-based method is described which defines a rigid transformation between two co-ordinate systems that reduces the accuracy requirements on the quality of the data-set (including, but not restricted to, the error in the acquisition process, and the number and spread of the points) measured in one of the two co-ordinate systems by identifying a set of remote correspondences that are used to bind the convergence process. The method can be used in minimal-access orthopaedic surgery to improve the accuracy of limb registration. Specific instances include femoral registration, by estimating the functional center of the hip joint in both co-ordinate systems to be co-registered, and tibial registration, using the ankle center as a distant set of paired correspondences. Accuracy can be measured in a variety of ways, including, but not restricted to, evaluating the mis-alignment between the two co-registered objects.

10 Claims, 2 Drawing Sheets

(56) References Cited

OTHER PUBLICATIONS

Ellis et al, "A method for evaluating CT-based surgical registration.", First joint conference computer vision, virtual reality and robotics in medicine and medical robotic and computer—assisted surgery, 1997, Issue 1205: 141-150.

Ellis et al, "Use of a biocompatible fiducial marker in evaluating the accuracy of computed tomograhpy image registration.", Investigative radiology, 1996, 31(10): 658-667.

Maintz et al., "A survey of medical image registration.", Medical image analysis, 1998, 2(1): 1-36.

Reinhardt et al., "Computer aided surgery with special focus on neuronavigation.", Computerized medical imaging and graphics, 1999, 23(5):237-244.

Simon et al., "Accuracy validation in image-guided orthopaedic surgery.", Proceedings of the second international symposium on medical robotics and computer assisted surgery, 1995, Baltimore: 185-192.

Tang et al., "Fiducial registration from a single X-Ray image: A new technique for fluoroscopic guidance and radiotherapy.", Medical image computing and computer-assisted intervention -MICCAI-2000, 1935:502-511.

Simon et al., "Medical imaging and registration in computer assisted surgery.", Clinical orthopaedics and related research, Philadelphia, Sep. 1998, vol. 354, p. 17-27.

Palombara et al., "Minimally invasive 3D data registration in computer and robot assisted total knee arthroplasty.", Medical and biological engineering and computing, Nov. 1997, vol. 35, No. 6.

Lea et al., "Registration and immobilization in robot-assisted surgery". Journal of Image Guided Surgery 1 (2), pp. 80-87, 1995 (11 pages).

\* cited by examiner

MODEL-BASED POSITIONAL ESTIMATION METHOD

This application is a continuation of U.S. application Ser. No. 11/718,662 filed Nov. 3, 2005, which is the national stage of PCT/GB2005/004249 filed Nov. 3, 2005, which claims priority to GB0424375.4 filed Nov. 4, 2004, the disclosures of which are incorporated in their entirety by reference herein.

The present invention relates to a model-based positional estimation method, and in particular although not exclusively to a method for mapping a plurality of measured points on a bone surface onto a corresponding bone model. The method finds particular although not exclusive application in minimal access orthopaedic surgery, to improve the accuracy of registration.

Registration can be defined as the determination of a one-to-one mapping between the two or three dimensional co-ordinates in one co-ordinate system and those in another, such that the points in the two spaces which correspond to the same feature are matched to each other. Registration also means the determination of the mapping operation that can transform one object from its space into the space of the other, whether in two or three dimensions. When the transformation has been determined to a desired accuracy, the objects are said to be registered, and may then be compared or superimposed to give one co-registered object.

Registration is an unavoidable step in virtually any procedure where different data-sets, whether generated by the same technology (also known as modality) at different times and circumstances, or by different technology altogether, need to be compared or contrasted. This process is necessary for a number of applications, spanning from diagnostics and statistical studies, to intra-operative image guidance and robotic-assisted surgery (Maintz and Viergever 1998; Reinhardt, Trippel et al. 1999).

In medical imaging, the modality or modalities involved in registration highlight the vast amount of techniques and methods available, ranging from diagnostic and treatment, to surgical intervention. Four classes of registration tasks can be recognised based on the modalities involved: mono-modal, multi-modal, modality to model, and patient to modality. In mono-modal applications, both images to be registered have been generated using the same technology, for example computed tomography (CT) or magnetic resonance (MR) imaging. Among these are a variety of diagnostic systems, where different images acquired at different intervals or circumstances with the same modality need to be compared and contrasted.

Multi-modal applications involve the registration of two images that have been generated utilising different modalities. An example of this category in medical imaging involves the registration process required to blend MR and CT images for complex procedures. This process is required to adequately visualise both the soft tissue from the former data set, and the hard tissue, which is more evident in the high-density CT images.

Modality to model methods involve the registration of images acquired with one modality to be registered against a standard anatomical model. These methods can be applied in gathering statistics on tissue morphology, and segmentation tasks, where the acquired image dataset is mapped against models of standard anatomy.

Patient to modality involves the registration of patient-specific anatomy with an image acquired using one of many modalities. It is usually associated with intra-operative registration, and intervention, e.g. radiotherapy, where the actual position of the patient needs to be known with respect to a pre-operative or previously acquired image. Even though the acquisition of patient-specific information may itself involve the use of a modality, the purpose of the process is to register the patient's position against the model. The two co-ordinate systems to be registered belong to the patient and to the modality used to acquire the registration image, respectively. This differs from multi-modal applications, where the two co-ordinate systems belong to two modalities, irrespective of the patient.

Computer Aided Surgery (CAS) generally involves patient to modality registration, as, in any CAS application that involves planning, the relationship between the modelled space, where the procedure is planned, and the patient's workspace, where the procedure is executed, needs to be established. Identifiable features, such as fiducial marker screws (Simon, O'Toole et al. 1995; Ellis, Toksvig-Larsen et al. 1996; Ellis, Fleet et al. 1997; Tang, Ellis et al. 2000) or anatomical landmarks (Lea, Watkins et al. 1995), are first extracted from the model and then "sensed," or located, in the operating theatre. This process provides the system with enough positional information for the modelled space and patient's space to be registered against a common coordinate system.

When access to the registration surface is restricted, such as in minimally-invasive surgery, registration accuracy can degenerate. This is due to the poor quality of the information collected in real space, both in terms of positional accuracy and surface covered, which results in poor correlation between the surfaces to be co-registered.

The present invention will be referred to as the "Bounded Registration Method". According to the invention there is provided a method of registering a measurement co-ordinate system to a model co-ordinate system, comprising:

measuring in the measurement co-ordinate system the location of a plurality of points within a local region, each said point having a corresponding model point location within the model co-ordinate system; and fitting the measured points to the corresponding model points subject to the constraint of one or more correspondences between the measurement and model co-ordinate systems at a location remote from the local region.

Let "C1" describe a set of two or three dimensional co-ordinates measured in co-ordinate system "1", and let "C2" describe the same set of co-ordinates in co-ordinate system "2". The aim of registration is to define a rigid transformation that accurately maps C1 into C2. The Bounded Registration method reduces the accuracy requirements on the quality of the data-set (including, but not restricted to, the error in the acquisition process, and the number and spread of the points) measured in one of the two co-ordinate systems by identifying a set of remote correspondences that are used to bind the convergence process.

Specifically, this method can be used in minimal-access orthopaedic surgery to improve the accuracy of limb registration. Specific instances include femoral registration, by estimating the functional centre of the hip joint in both co-ordinate systems to be co-registered, and tibial registration, using the ankle centre as a distant set of paired correspondences. Accuracy can be measured in a variety of ways, including, but not restricted to, evaluating the mis-alignment between the two co-registered objects.

The Bounded Registration method binds the outcome of model-based registration by means of a remote set of paired correspondences (one or many depending upon the application and the angles to be bound) in the two spaces to be co-registered. The remote set of paired correspondences can include the centre or axis of a joint.

The invention extends to any and all of the following:

A method to bind the outcome of model-based registration and reduce the accuracy requirements on the quality of the data-set by means of a remote set of paired correspondences in the two spaces to be co-registered.

A method as in Clause 1, where the remote correspondence can be one or many.

A method as in Clause 1, where the minimisation process cam be adapted to use one of many available algorithms.

A method as in Clause 1, where the accuracy of registration is both proportional to, and bound by, that obtained for the remote paired correspondences.

A method as in Clause 1, where the remote set of correspondences can be generated by identifying the centre or axis of a joint.

A method as in Clause 5, where the joint centre can be sensed with a number of techniques, including, but not restricted to, moving the bone around a relevant joint to estimate the joint centre, and using devices such as a mechanical digitizer, an optical tracker, an electromagnetic tracker, or ultrasound probe.

A method as in Clause 5, where the object to be registered is a body part such as a femur, tibia, humerus, radius or ulna.

A method as herein described and illustrated in the accompanying drawings.

A preferred embodiment of the invention will now be described with reference to the accompanying drawings in which.

The Bounded Registration method's preferred embodiment involves minimal-access femoral registration for computer-assisted knee arthroplasty.

Figure 1:
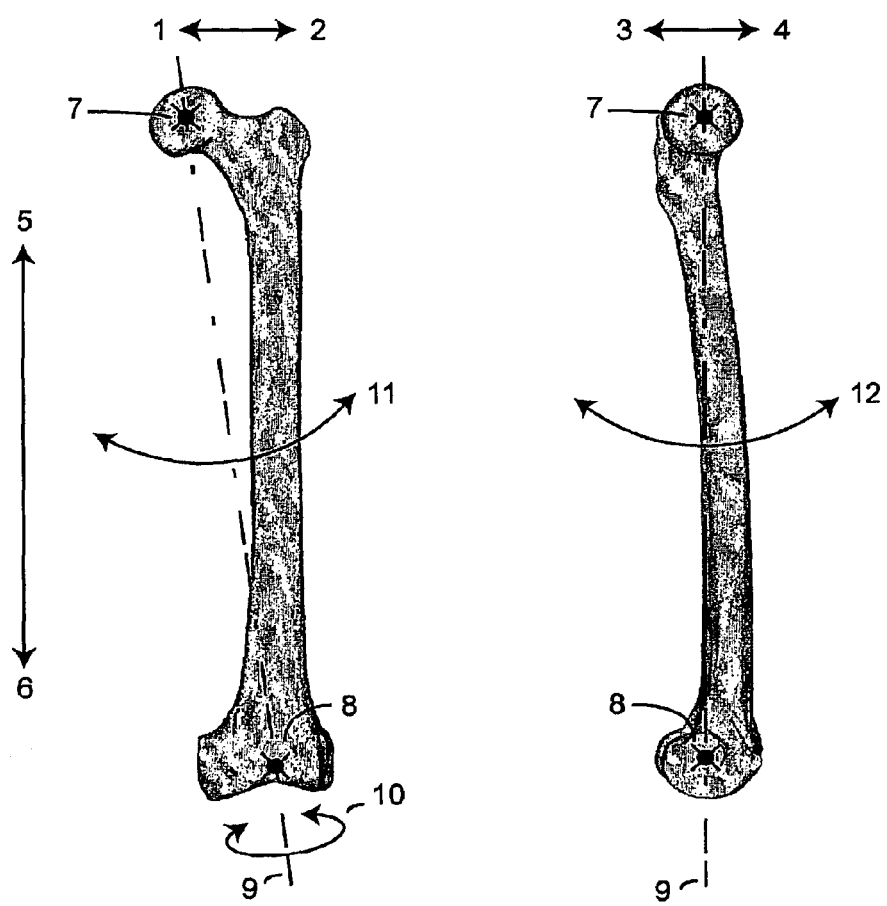
FIG. 1 shows two views of a femur and the femur alignment in terms of knee and hip centres.

As illustrated in FIG. 1, let leg placement be defined according to anatomical notation, using the medial 1, lateral 2, posterior 3, anterior 4, proximal 5 and distal 6 nomenclature. Also, let correct varus/valgus 11 and anterior/posterior 12 alignment of the mechanical axis 9 be specified by defining the position of the knee, which can be approximated by a single set of 3D co-ordinates situated anywhere on the distal femur 8, and the centre of the femoral head 7.

Figure 2:
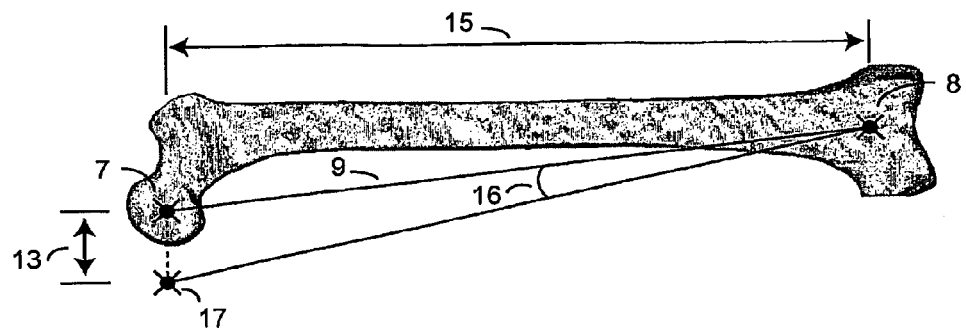
FIG. 2 shows a trigonometrical model characterising the effect of the error of the hip centre estimate on the overall alignment of the femur.

Accurately estimating the centre of the femoral head 7 provides a three dimensional point that is very far from the distal femur where the data-set for registration is collected. As illustrated in FIG. 2, a medial displacement error 13 of 1 cm in the true hip centre 7 to an estimate 17 will result in less than 1.3□ of varus/valgus misalignment 16, assuming a 40 cm average length of femur 15 and correct distal alignment. Therefore, correctly locating the position of the functional centre of the hip 7 has the potential to guarantee correct anterior/posterior 12 and varus/valgus alignment 11 of the leg. The hip centre 7 can be sensed with a number of techniques, including, but not restricted to, pivoting the leg about the acetabulum and estimating the hip centre, and using devices such as a mechanical digitizer, an optical tracker, or ultrasound probe.

The Bounded Registration method is designed to harvest the full potential from the hip centre, without impairing correct registration of the degrees of freedom, such as axial rotation 10, and medial 1, lateral 2, posterior 3, anterior 4, proximal 5 and distal 6 translations, which do not influence the alignment of the mechanical axis 9.

Figure 3:
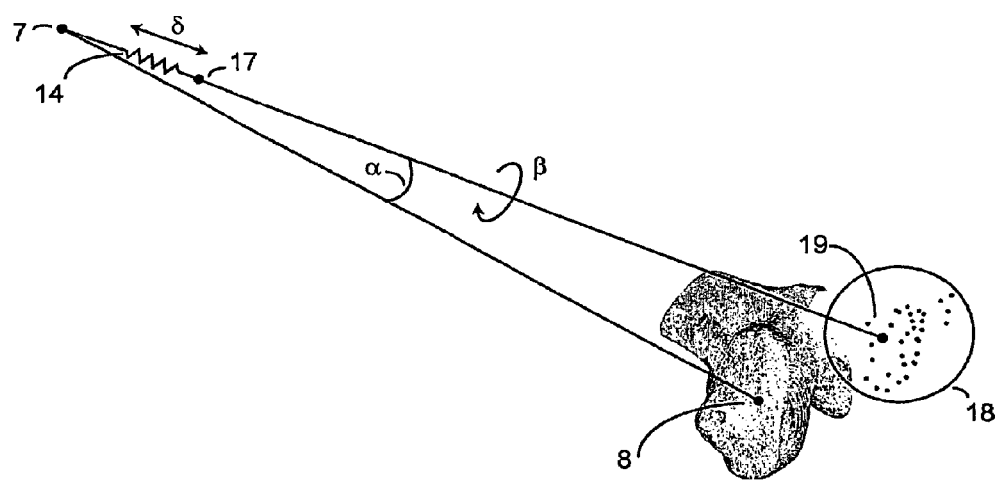
FIG. 3 depicts a physical model for the convergence of the Bounded Registration method.

The method is outlined for the femur and it is based on pre-operatively acquired data. A "physical" model for the convergence process is used for illustrative purposes (FIG. 3). To simplify the description, it is assumed that both modelled 7 and estimated 17 hip centres can be accurately defined.

Initially, the modelled 7 and estimated 17 hip centre positions (which are in model and real space respectively) are considered to be coincident. All points 18 measured on the distal femur within a local region 18 are regarded as a whole, by referring to them in terms of their centroid—the "knee centre estimate" 19. Finally, the knee centre estimate 19 is connected to the modelled hip centre 7 with a virtual spring or slider 14, able to extend and compress, but not bend.

Each point has a corresponding representation on the modelled surface, which needs to be correctly identified for the best solution to be found. Pairs of points and respective closest points provide the error measure to be minimised, which can be expressed in terms of the Root Mean Square (RMS) of their relative distance, and is used in the error minimisation process until a solution is found (e.g. the error falls below a specified threshold). Other error measures could of course be used.

The distal point-set 18 is allowed to rotate about the modelled hip centre 7 ($\alpha$), to move away or toward the modelled hip centre 7 ($\delta$) and to rotate about the axis defined by the knee centre estimate 19 and modelled hip centre 7 ($\beta$). In this embodiment, a possible solution, or local minimum, is obtained for the position of the point-set on the modelled surface where the error measure between points and closest points is minimum.

Alternatively, where the points are well-defined, and the model points corresponding to the measurements can be regarded as known, the error measure may be calculated as the RMS error of the distance between model and actual point locations.

In the preferred embodiment, minimisation is carried on the RMS value of the distances between the measured points and the model surface, with the values of $\alpha$, $\beta$ and $\delta$ being "free" and allowed to vary in an unrestrained manner.

In this embodiment, convergence of the Bounded Registration method is achieved by iterating upon closest points (Besl and McKay 1992), where the transformation matrix used to map the points onto the surface at every iteration is calculated by applying rotations about and translations along the axis generated by the hip centre and centroid of the point-set. Successive transformations applied to the original point-set are therefore bound at one end while free to move at the other, giving the Bounded Registration method its name. The minimisation process can be adapted to use one of many available algorithms.

While a specific embodiment of the present invention has been described, it will be apparent to those skilled in the art that various modifications thereto can be made without departing from the spirit and scope of the invention as defined in the appended claims. For instance, the method can be applied to tibial registration by replacing the femur with the tibia and the hip centre with a feature on the ankle joint. The technique can also be applied to the upper limb and other body parts in a similar manner.

In the previously described technique, it is not essential for all of the variables $\alpha$, $\beta$ and $\delta$ to be left "free". Other possibilities could be envisaged, for example by constraining the value of $\delta$ to be equal to 0 (in other words, constraining the modeled 7 and estimated 17 positions to be coincident). The minimization may be carried out subject to the constraint of one or more remote correspondences, and it is specifically anticipated that in some applications there may be multiple correspondences/constraints which are located at a variety of different remote locations. These may optionally be combined with one or more axial constraints.

REFERENCES

Besl, P. J. and N. D. McKay (1992). "A method for registration of 3-D shapes." IEEE Transactions on Pattern Analysis and Machine Intelligence 14(2): 239-256.

Ellis, R. E., D. J. Fleet, et al. (1997). "A method for evaluating CT-based surgical registration." CVRMed-MRCAS'97: First Joint Conference Computer Vision, Virtual Reality and Robotics in Medicine and Medical Robotics and Computer-Assisted Surgery. J. Troccaz, E. Grimson and R. Moesges, Springer Verlag Kg. Issue 1205: 141-150.

Ellis, R. E., S. Toksvig-Larsen, et al. (1996). "Use of a biocompatible fiducial marker in evaluating the accuracy of Computed Tomography image registration." Investigative Radiology 31(10): 658-667.

Maintz, J. B. A. and M. A. Viergever (1998). "A survey of medical image registration." Medical Image Analysis 2(1): 1-36.

Reinhardt, H., M. Trippel, et al. (1999). "Computer aided surgery with special focus on neuronavigation." Computerized Medical Imaging and Graphics 23(5): 237-244.

Simon, D. A., R. V. O'Toole, et al. (1995). "Accuracy validation in Image-Guided orthopaedic surgery." Proceedings of the Second International Symposium on Medical Robotics and Computer Assisted Surgery, Baltimore: 185-192.

Tang, T. S. Y., R. E. Ellis, et al. (2000). "Fiducial registration from a single X-Ray image: A new technique for fluoroscopic guidance and radiotherapy." Medical Image Computing and Computer-Assisted Intervention—MICCAI 2000. S. L. Delp, A. M. DiGioia and B. Jaramaz, Springer-Verlag. 1935: 502-511.

The invention claimed is:

1. A method of registering a bone measurement coordinate system to a computer bone model coordinate system, comprising:
measuring in the bone measurement coordinate system the location of a plurality of points at a registration surface of the bone, each said point having a corresponding model point location within the computer bone model coordinate system; and
fitting the measured points to the corresponding model points using a processor of a computing system, wherein the processor is configured to apply one or more manipulation on an axis generated between the measured points and a common remote point, remote from the bone registration surface, in the bone measurement and computer bone model coordinate systems,
wherein the one or more manipulation is at least one of a rotation of the measured points about the axis, a translation along the axis, or a rotation of the axis about the common remote point.

2. A method as claimed in claim 1 in which the fitting comprises minimizing an error measure between the measured points and the model points.

3. A method as claimed in claim 1 in which the fitting is carried out leaving a distance between the registration surface and the remote point as a free variable.

4. A method as claimed in claim 1 in which the correspondence comprises an axis which is constrained to extend from the registration surface to the common remote point.

5. A method as claimed in claim 4 in which the axis extends from a centroid of the measured points to the common remote point.

6. A method as claimed in claim 4 in which the fitting is carried out leaving an angle of rotation of the measured points about the axis as a free variable.

7. A method as claimed in claim 4 in which the fitting is carried out leaving a rotation angle of the axis about the remote point as a free variable.

8. A method as claimed in claim 1 in which the common remote point is the center of a joint of the bone and in which the joint center is measured in the bone measurement coordinate system by moving the bone about the joint.

9. A method as claimed in claim 1 in which the correspondence comprises an axis which is constrained to extend from the accessible bone registration surface to the common remote point and in which the said axis is an axis of a joint of the bone.

10. A method as claimed in claim 1 in which the bone is a femur, tibia, humerus, radius or ulna.

* * * * *